(12) United States Patent
Marta et al.

(10) Patent No.: US 9,136,084 B2
(45) Date of Patent: Sep. 15, 2015

(54) MICRO DISCHARGE DEVICES, METHODS, AND SYSTEMS

(71) Applicant: Honeywell International Inc., Morristown, NJ (US)

(72) Inventors: Teresa M. Marta, White Bear Lake, MN (US); Fouad Nusseibeh, Champlin, MN (US)

(73) Assignee: Honeywell International Inc., Morristown, NJ (US)

( * ) Notice: Subject to any disclaimer, the term of this patent is extended or adjusted under 35 U.S.C. 154(b) by 185 days.

(21) Appl. No.: 13/744,196

(22) Filed: Jan. 17, 2013

(65) Prior Publication Data

US 2014/0196520 A1 Jul. 17, 2014

(51) Int. Cl.
| | |
|---|---|
| *G01N 30/00* | (2006.01) |
| *H01J 5/16* | (2006.01) |
| *G01N 30/74* | (2006.01) |
| *G01N 30/64* | (2006.01) |
| *H01J 11/44* | (2012.01) |
| *G01N 27/68* | (2006.01) |
| *G01N 30/60* | (2006.01) |

(52) U.S. Cl.
CPC . *H01J 5/16* (2013.01); *G01N 30/64* (2013.01); *G01N 30/74* (2013.01); *H01J 11/44* (2013.01); *G01N 27/68* (2013.01); *G01N 30/6095* (2013.01)

(58) Field of Classification Search
CPC ....... G01N 27/68; G01N 30/00; G01N 30/64; G01N 30/74; G01N 30/6095; H01J 5/16; H01J 11/44

USPC ................................................. 73/23.35, 23.4
See application file for complete search history.

(56) References Cited

U.S. PATENT DOCUMENTS

| | | | |
|---|---|---|---|
| 7,100,421 B1 * | 9/2006 | Herring | 73/23.35 |
| 7,126,266 B2 * | 10/2006 | Park et al. | 313/495 |
| 7,142,303 B2 * | 11/2006 | Gianchandani et al. | 356/417 |
| 7,701,578 B1 * | 4/2010 | Herring | 356/417 |
| 7,910,896 B2 | 3/2011 | Marta et al. | |
| 8,196,449 B2 | 6/2012 | McBrady et al. | |
| 2004/0223882 A1 * | 11/2004 | Bonne et al. | 422/82.05 |
| 2004/0245993 A1 * | 12/2004 | Bonne | 324/464 |
| 2005/0142035 A1 * | 6/2005 | Bonne et al. | 422/82.05 |
| 2009/0031785 A1 * | 2/2009 | Kellner et al. | 73/23.39 |

OTHER PUBLICATIONS

Y.B. Gianchandani, et al, "Exploring microdischarges for portable sensing applications", Anal Bioanal Chem, Aug. 12, 2009 (17 pages).

* cited by examiner

*Primary Examiner* — Daniel S Larkin
(74) *Attorney, Agent, or Firm* — Brooks, Cameron & Huebsch, PLLC

(57) ABSTRACT

Micro discharge devices, methods, and systems are described herein. One device includes a non-conductive material, a channel through at least a portion of the non-conductive material having a first open end and a second open end, a first electrode proximate to a first circumferential position of the channel between the first open end and the second open end, a second electrode proximate to a second circumferential position of the channel between the first open end and the second open end, a discharge region defined by a portion of the channel between the first electrode and the second electrode, an optical emission collector positioned to receive an optical emission from the discharge region, and a discharge shielding component between the discharge region and the optical emission collector.

19 Claims, 3 Drawing Sheets

MICRO DISCHARGE DEVICES, METHODS, AND SYSTEMS

TECHNICAL FIELD

The present disclosure relates to micro discharge devices, methods and systems.

BACKGROUND

Micro discharge devices can be used in various applications including chemical sensing, for instance (e.g., as a part of a gas chromatograph (GC)). In operation, micro discharge devices can apply a voltage across a gas and create a plasma, thereby exciting electrons to higher energy levels. As the electrons return to lower energy levels, photons of light may be emitted at various wavelengths characteristic of particular atoms and/or molecules. Such emission can be received by an optical emission collector (e.g., optical fiber and/or optical transmission line) and used to determine a chemical composition of the gas, for instance.

However, previous micro discharge devices that incorporate an optical emission collector within and/or near a plasma of a micro discharge device may introduce contaminants into the gas. Additionally, in previous approaches, optical emission collectors may be prone to degradation and/or damage caused by the harsh environment associated with the plasma and/or gas(es).

DETAILED DESCRIPTION

Figure 1A:
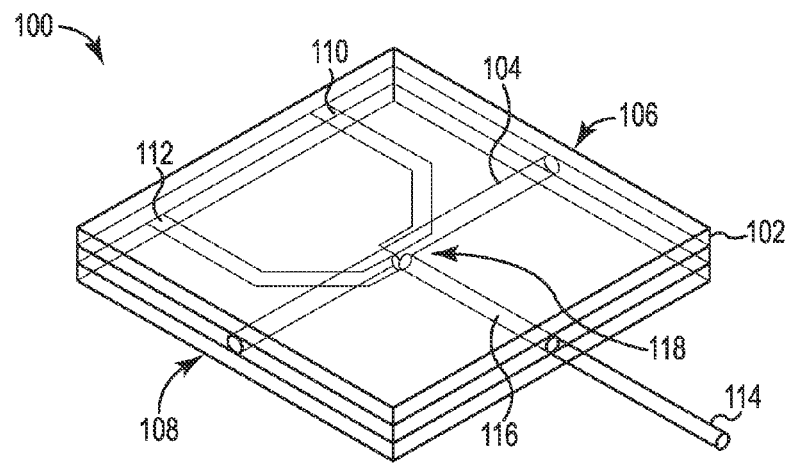
FIG. 1A is a perspective view of a micro discharge device in accordance with one or more embodiments of the present disclosure.

Micro discharge devices, methods, and systems are described herein. For example, one or more embodiments include a non-conductive material, a channel through at least a portion of the non-conductive material having a first open end and a second open end, a first electrode proximate to a first circumferential position of the channel between the first open end and the second open end, a second electrode proximate to a second circumferential position of the channel between the first open end and the second open end, a discharge region defined by a portion of the channel between the first electrode and the second electrode, an optical emission collector positioned to receive an optical emission from the discharge region, and a discharge shielding component between the discharge region and the optical emission collector.

Micro discharge devices in accordance with one or more embodiments of the present disclosure can include a discharge shielding component (e.g., barrier) between an optical emission collector (e.g., optical fiber) and potentially harmful gas(es) and/or plasma(s). Accordingly, embodiments of the present disclosure can reduce degradation of optical fibers. Reduction in degradation can yield improved measurements and/or longer lifespan, for instance. Further, a discharge shielding component can reduce (e.g., prevent) potential contaminations caused by an optical emission collector's presence within and/or near a plasma of a micro discharge device as in previous approaches.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits.

As used herein, "a" or "a number of" something can refer to one or more such things. For example, "a number of blocks" can refer to one or more blocks.

Figure 1B:
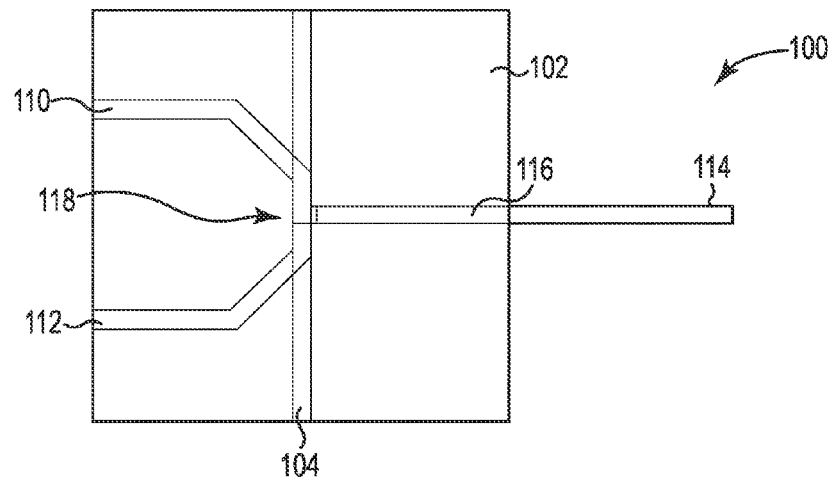
FIG. 1B is an overhead view of the micro discharge device illustrated in FIG. 1A.
Figure 1C:
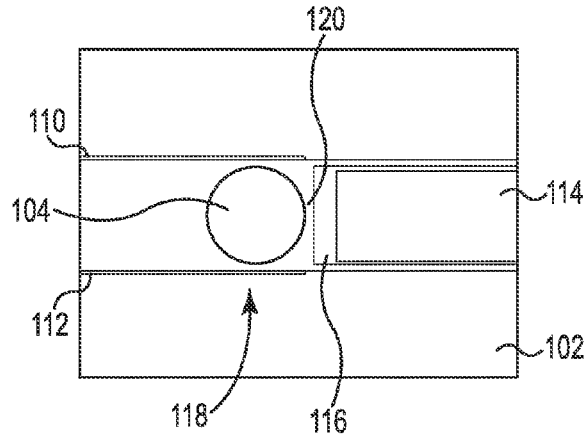
FIG. 1C is a side view of a portion of the micro discharge device illustrated in FIG. 1A and FIG. 1B.

FIG. 1A is a perspective view of a micro discharge device 100 in accordance with one or more embodiments of the present disclosure. Micro discharge device 100 is sometimes generally referred to herein as "device 100." As discussed further below, FIGS. 1A, 1B, and 1C illustrate device 100 from different points of view (e.g., perspective, overhead, and cross-sectional, respectively). FIGS. 1A, 1B, and 1C are sometimes cumulatively referred to herein as "FIG. 1."

As shown in FIG. 1A, device 100 includes a body 102, a gas channel 104 therethrough, opening at a gas channel port 106 and a gas channel port 108 (e.g., open ends of gas channel 104). As shown in the embodiment illustrated in FIG. 1, gas channel port 106 and gas channel port 108 can be on opposing faces of body 102. As shown in FIG. 1A, device 100 can include a top electrode 110, a bottom electrode 112, and an optical fiber channel 116 into which an optical emission collector 114 can be positioned. Optical emission collector 114 is sometimes generally referred to herein as "optical fiber 114."

Body 102 can be and/or include one or more dielectric and/or non-conductive (e.g., electrically non-conductive) materials such as glass, silica, plastic, quartz, ceramic, etc. that resist etching from plasma. As shown in FIG. 1A and FIG. 1C, body 102 can include a plurality of (e.g., 3) layers. Such layers can be affixed to each other by various means, for instance, though embodiments are not limited to the inclusion of layers in body 102, nor are embodiments limited to a particular number of layers, if included. Body 102 (e.g., portions of body 102) can be substantially transparent, for instance (e.g., allowing greater than 90% transmittance of light at wavelengths of 400 nanometers).

Gas channel 104 can be defined in body 102 by photolithography, for instance, and/or formed by various techniques (e.g., etching). For example, gas channel 104 can be formed by etching two layers of body 102 (previously discussed), aligning the two layers, and laminating (e.g., fusing) the two layers together. Gas channel 104 can be of various diameters. For example, a diameter of gas channel 104 can be between 350-400 microns.

Top electrode 110 and bottom electrode 112 can be formed, for instance, by masking and coating metal traces (e.g., gold) on opposing surfaces of portions of body 102. Top electrode 110 and/or bottom electrode 112 can be of various thicknesses and/or widths. For example, top electrode 110 and/or bottom electrode 112 can be between 3 and 6 microns thick and/or between 350 and 400 microns wide, though embodiments of the present disclosure do not limit electrode thickness and/or width to particular ranges.

In the embodiment shown in FIG. 1, for instance, top electrode 110 and bottom electrode 112 are shown on opposing surfaces of a middle layer of body 102, though embodiments of the present disclosure are not so limited. For example, as previously discussed, body 102 can include other number(s) of layer(s), for instance. It is noted that "top" and "bottom" are used only for descriptive purposes and are intended to convey substantially opposing positions of electrodes with respect to a portion gas channel 104 (e.g., as shown in FIG. 1C). For instance, top electrode 110 can be considered proximate to a first circumferential position of gas channel 104. Similarly, bottom electrode 112 can be considered proximate to a second circumferential position of gas channel 104.

Optical fiber channel 116 can be defined in body 102 by photolithography, for instance, and/or formed by various techniques (e.g., etching) in a manner analogous to gas channel 104. For example, a diameter of optical fiber channel 116 can be formed by etching two layers of body 102 (previously discussed), aligning the two layers, and laminating the two layers together. Optical fiber channel 116 can be of various diameters. For example, optical fiber channel 116 can be between 350-400 microns. Optical fiber 114 can be a plastic and/or glass optical fiber and can be positioned within (e.g., within a portion of) optical fiber channel 116.

FIG. 1B is an overhead view of the micro discharge device 100 illustrated in FIG. 1A. As shown in FIG. 1B, body 102 can be substantially square and/or rectangular, though embodiments of the present disclosure are not limited to particular shape(s). For example, a width of a major surface of body 102 can be in a range of 1 centimeter square to 5 centimeters squared, and a thickness (e.g., width of minor side) of body 102 can be in a range of 1 millimeter to 2 millimeters. As shown in FIG. 1B, top electrode 110 and bottom electrode 112 can overlap (e.g., a portion of top electrode 110 can overlap a portion of bottom electrode 112). Further, as shown, gas channel 104 can be substantially perpendicular to optical fiber channel 116 and/or optical fiber 114, in some embodiments.

FIG. 1C is a side view of a portion of the micro discharge device 100 illustrated in FIG. 1A and FIG. 1B. FIG. 1C illustrates a discharge region 118 of gas channel 104. Discharge region 118 can be a portion of gas channel 104 between top electrode 110 and bottom electrode 112. As shown in FIG. 1C, top electrode 110 and bottom electrode 112 can each be located a particular distance from discharge region 118 of gas channel 104. That is, a particular thickness of body 102 can separate each of top electrode 110 and bottom electrode 112 from gas channel 104. Such a distance can be selected based on desired protective level of top electrode 110 and/or bottom electrode 112 from potentially harmful plasma formed in discharge region 118, for instance. For example, such a thickness can be between 1 and 15 microns.

As shown in FIG. 1C, top electrode 110 and bottom electrode 112 can be embedded within body 102 (e.g., between layer(s) of body 102). In various embodiments, top electrode 110 and/or bottom electrode 112 can be positioned on an outer surface of body 102.

As shown in FIG. 1C, optical fiber 114 can be positioned to receive an optical emission from discharge region 118 (e.g., proximate to discharge region 118) A discharge shielding component 120 (e.g., barrier) can be positioned between discharge region 118 and optical fiber 114. Discharge shielding component 120 can protect optical fiber 116 from discharge(s) in discharge region 118. That is, discharge shielding component 120 can protect optical fiber 116 from potentially harmful gas(es), particulate matter, and/or plasma present in discharge region 118, for instance. Accordingly, discharge shielding component 120 can be and/or include materials analogous to that used in portions of body 102 (e.g., glass, silica, plastic, quartz, ceramic, etc.). Discharge shielding component 120 (e.g., a portion of discharge shielding component 120) can be substantially transparent.

Discharge shielding component 120 can be incorporated as a part of a structure of device 100. For example discharge shielding component 120 can be a particular portion (e.g., thickness) of body 102 between discharge region 118 and an interior terminal end of optical fiber channel 116 (e.g., in a range of 20 to 50 microns).

Discharge shielding component 120 can be various components independent of body 102. For example, discharge shielding component 120 can be and/or include a substantially flat window. Discharge shielding component 120 can be and/or include a lens. Discharge shielding component 120 can be and/or include a mirror (e.g., as illustrated in FIG. 3C). Such components can be positioned within optical fiber channel 116. Such components can be positioned between optical fiber 114 and discharge region 118. Such components can be positioned to create a seal preventing gas and/or plasma from passing from discharge region 118 to optical fiber 114. Such components can be of various thicknesses. For example, such components can be of thicknesses ranging from 20 to 50 microns.

A gas can enter gas channel 104 via gas channel port 106 and/or gas channel port 108. Thereafter, the gas can pass through discharge region 118 (e.g., between top electrode 110 and bottom electrode 112) where a voltage can be applied using top electrode 110 and bottom electrode 112 (e.g., a voltage can be applied across top electrode 110 and bottom electrode 112). Such a voltage can range from 400 to 2,000 volts, for example. Such a voltage can be applied using alternating current up to 200 kilohertz, for example.

The voltage applied using top electrode 110 and bottom electrode 112 can create a plasma in discharge region 118 from the gas, thereby exciting electrons of the gas to higher energy levels, for instance. As the electrons return to lower energy levels, an optical emission can be created (e.g., photons of light can be emitted). The optical emission can pass through discharge shielding component 120 and can be received by optical fiber 114. Thereafter, the gas can exit device 100 though gas channel port 106 and or gas channel port 108.

Once received by optical fiber 114, the optical emission can travel along a length of optical fiber 114 and be received by a receiver. The receiver can be a device configured to convert the optical emission into an electric signal. Such a device can be and/or include, for example, an image sensor and/or a photodiode array, among others. In an example, the receiver can include a plurality of photodiodes, each photodiode being filtered to receive a particular (e.g., unique and/or narrow) portion (e.g., bandwidth) of the optical emission and convert that portion to a respective electric signal. A computing device can use processing resources to execute instructions stored in memory to receive the electric signal(s) and determine a composition associated with the gas based on the electric signal(s), for instance.

Figure 2A:
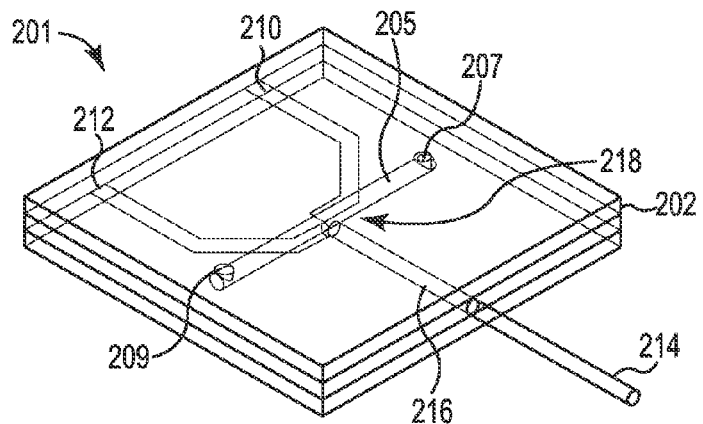
FIG. 2A is a perspective view of a micro discharge device in accordance with one or more embodiments of the present disclosure.
Figure 2B:
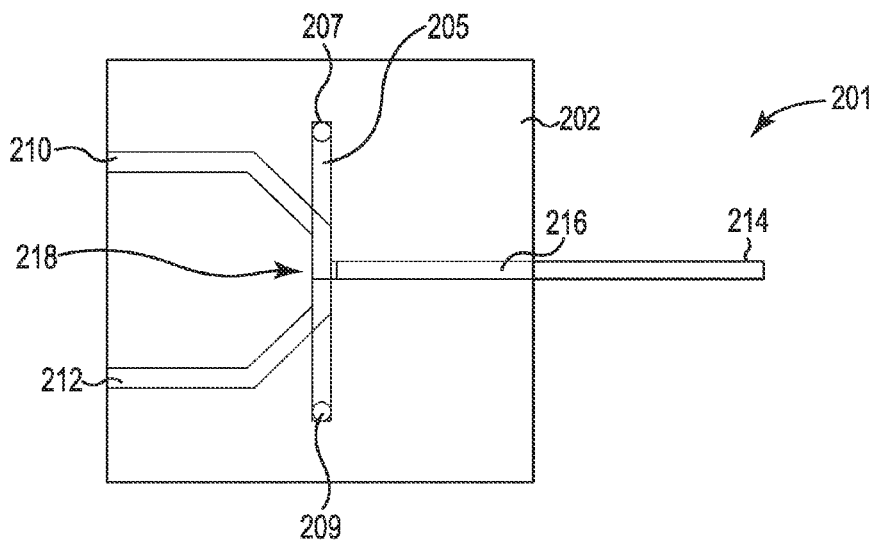
FIG. 2B is an overhead view of the micro discharge device illustrated in FIG. 2A.
Figure 2C:
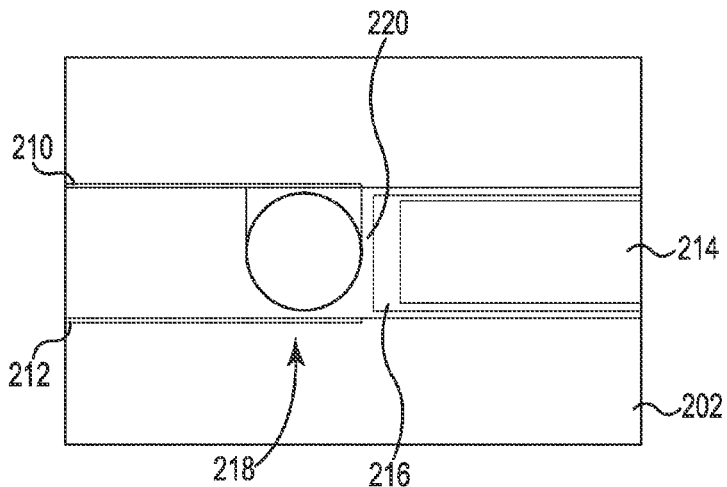
FIG. 2C is a side view of a portion of the micro discharge device illustrated in FIG. 2A and FIG. 2B.

FIG. 2A is a perspective view of a micro discharge device 201 in accordance with one or more embodiments of the present disclosure. FIG. 2B is an overhead view of the micro discharge device 201 illustrated in FIG. 2A. FIG. 2C is a side view of a portion of the micro discharge device 201 illustrated in FIG. 2A and FIG. 2B. Micro discharge device 201 is sometimes generally referred to herein as "device 201." FIGS. 2A, 2B, and 2C are sometimes cumulatively referred to herein as "FIG. 2."

As shown in FIG. 2, device 201 includes a body 202, a gas channel 205 through a portion thereof, opening at a gas channel port 207 and a gas channel port 209 (e.g., open ends of gas channel 205). As shown in the embodiment illustrated in FIG. 2, gas channel port 207 and gas channel port 209 can be on a same face (e.g., top) of body 202. In a manner analogous to device 100 previously discussed in connection with FIG. 1, device 201 can include a top electrode 210, a bottom electrode 212, and an optical fiber channel 216 into which an optical emission collector 214 (e.g., optical fiber 214) can be positioned.

Gas channel port 207 and/or gas channel port 209 can be vias, for instance, in body 202 (e.g., formed during a masking step of manufacture of device 201). A gas can enter gas channel 205 via gas channel port 207 and/or gas channel port 209. Thereafter, the gas can pass through discharge region 218 (e.g., between top electrode 210 and bottom electrode 212) where a voltage can be applied using top electrode 210 and bottom electrode 212. Such a voltage can range from 400 to 2,000 volts, for example. Such a voltage can be applied using alternating current up to 200 kilohertz, for example.

The voltage applied using top electrode 212 and bottom electrode 212 can create a plasma in discharge region 218 from the gas, thereby exciting electrons of the gas to higher energy levels, for instance. As the electrons return to lower energy levels, photons of light can be emitted. The photons can pass through discharge shielding component 220 and can be received by optical fiber 214. Thereafter, the gas can exit device 201 though gas channel port 207 and or gas channel port 209.

Figure 3A:
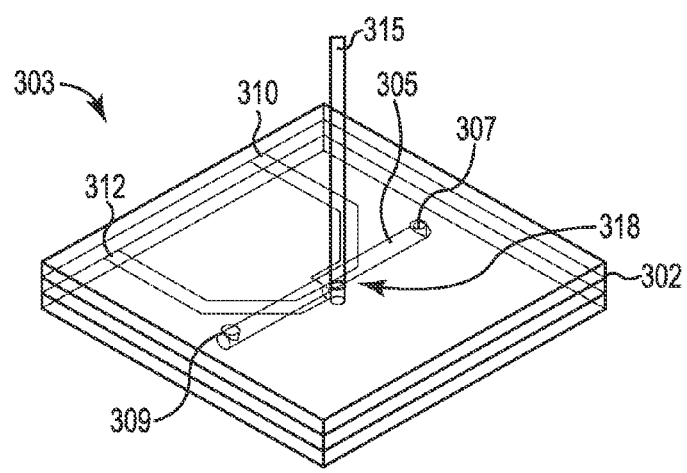
FIG. 3A is a perspective view of a micro discharge device in accordance with one or more embodiments of the present disclosure.
Figure 3B:
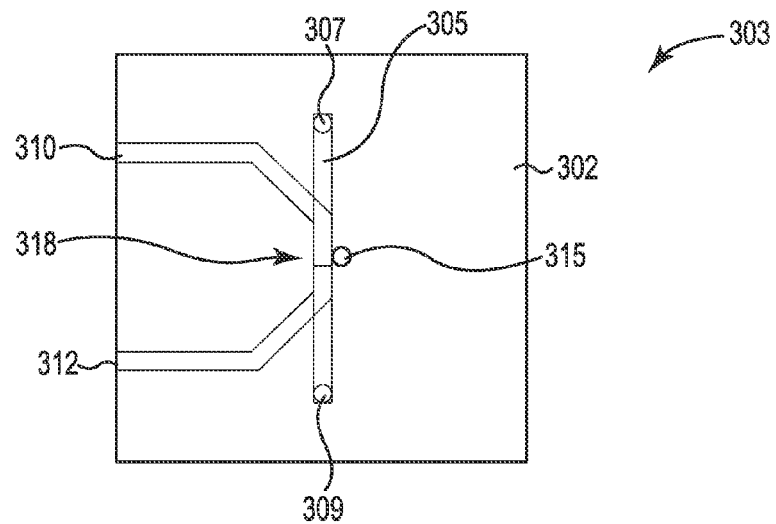
FIG. 3B is an overhead view of the micro discharge device illustrated in FIG. 3A.
Figure 3C:
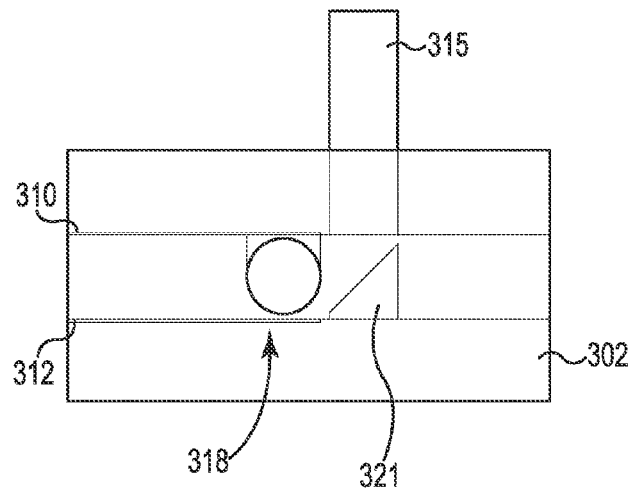
FIG. 3C is a side view of a portion of the micro discharge device illustrated in FIG. 3A and FIG. 3B.

FIG. 3A is a perspective view of a micro discharge device 303 in accordance with one or more embodiments of the present disclosure. FIG. 3B is an overhead view of the micro discharge device 303 illustrated in FIG. 3A. FIG. 3C is a side view of a portion of the micro discharge device 303 illustrated in FIG. 3A and FIG. 3B. Micro discharge device 303 is sometimes generally referred to herein as "device 303." FIGS. 3A, 3B, and 3C are sometimes cumulatively referred to herein as "FIG. 3."

As shown in FIG. 3, device 303 includes a body 302, a gas channel 305 through a portion thereof, opening at a gas channel port 307 and a gas channel port 309 (e.g., open ends of gas channel 305). As shown in the embodiment illustrated in FIG. 3, and in a manner analogous to device 201 previously discussed in connection with FIG. 2, gas channel port 307 and gas channel port 309 can be on a same face (e.g., top) of body 302. In a manner analogous to devices 100 and 201, previously discussed in connection with FIGS. 1 and 2, respectively, device 303 can include a top electrode 310 and a bottom electrode 312.

As shown in FIG. 3, device 303 can include an optical emission collector 315 (e.g., optical fiber 315). As shown, optical fiber 315 can be positioned substantially perpendicular to a longitudinal axis of gas channel 305 in a first axial direction and a second axial direction. Such a positioning can be contrasted, for example, with optical fiber 114 illustrated in FIG. 1 as being substantially perpendicular to a longitudinal axis of gas channel 104 in a single axial direction. Optical fiber 315 extends through a top face of body 302 (e.g., through a via in body 302).

As shown in FIG. 3, device 303 includes a discharge shielding component 321. As shown, discharge shielding component 321 can be and/or include a mirror (e.g., a metalized and/or non-conductive reflective surface). Such a mirror can be positioned to reflect photons of light towards optical fiber 315, for instance.

A gas can enter gas channel 305 via gas channel port 307 and/or gas channel port 309. Thereafter, the gas can pass through discharge region 318 (e.g., between top electrode 310 and bottom electrode 312) where a voltage can be applied using top electrode 310 and bottom electrode 312. Such a voltage can range from 400 to 2,000 volts, for example. Such a voltage can be applied using alternating current up to 200 kilohertz, for example.

The voltage applied using top electrode 310 and bottom electrode 312 can create a plasma in discharge region 318 from the gas, thereby exciting electrons of the gas to higher energy levels, for instance. As the electrons return to lower energy levels, photons of light can be emitted. The photons can pass through a substantially transparent portion of discharge shielding component 321 and can thereafter be reflected by a mirror portion of discharge shielding component 321 towards optical fiber 315 for reception by optical fiber 315. Thereafter, the gas can exit device 303 though gas channel port 307 and or gas channel port 309.

As previously discussed, discharge shielding component 321 can be positioned in a manner analogous to discharge shielding component 120 previously discussed in connection with FIG. 1, to create a seal preventing gas and/or plasma from passing from discharge region 318 to optical fiber 315.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A micro discharge device, comprising:
a non-conductive material;
a channel through at least a portion of the non-conductive material having a first open end and a second open end;
a first electrode separated from a first circumferential position of the channel by a particular thickness of the non-conductive material between the first open end and the second open end;
a second electrode separated from a second circumferential position of the channel by a particular thickness of the non-conductive material between the first open end and the second open end;
a discharge region defined by a portion of the channel between the first electrode and the second electrode;
an optical emission collector positioned to receive an optical emission from the discharge region; and
a discharge shielding component between the discharge region and the optical emission collector.

2. The device of claim 1, wherein the first open end is on a first face of the non-conductive material and the second open end is on a second face of the non-conductive material, and wherein the first face opposes the second face.

3. The device of claim 1, wherein the first open end and the second open end are on a same face of the non-conductive material.

4. The device of claim 1, wherein a longitudinal axis of the optical emission collector is substantially perpendicular to a longitudinal axis of the channel in an axial direction.

5. The device of claim 1, wherein a longitudinal axis of the optical emission collector is substantially perpendicular to a longitudinal axis of the channel in a first axial direction and a second axial direction.

6. The device of claim 1, wherein the optical emission collector extends through a first face of the non-conductive material, and wherein the first open end is on a second face of the non-conductive material, and wherein the second open end is on a third face of the non-conductive material.

7. The device of claim 1, wherein the optical emission collector extends through a face of the non-conductive material, and wherein the first open end and the second open end are on the face of the non-conductive material.

8. The device of claim 1, wherein the discharge shielding component includes a substantially flat window.

9. The device of claim 1, wherein the discharge shielding component includes a mirror.

10. The device of claim 1, wherein the discharge shielding component includes a lens.

11. The device of claim 1, wherein at least a portion of the discharge shielding component is substantially transparent.

12. The device of claim 1, wherein the first electrode is separated from the first circumferential position of the channel by a first thickness of the non-conductive material, and wherein the second electrode is separated from the second circumferential radial position of the channel by a second thickness of the non-conductive material.

13. A method, comprising:
receiving a gas through one of:
a first open end of a channel through at least a portion of a non-conductive material; and
a second open end of the channel, wherein the channel passes between a first electrode and a second electrode, and wherein at least one of the first and second electrodes is separated from the channel by a particular thickness of the non-conductive material;
applying a voltage across a discharge region of the channel using the first electrode and the second electrode; and
receiving an optical emission from the discharge region with an optical emission collector separated from the discharge region by a discharge shielding component.

14. The method of claim 13, wherein the discharge shielding component includes a portion of the non-conductive material between the optical emission collector and the discharge region.

15. The method of claim 14, wherein the portion of the non-conductive material between the optical emission collector and the discharge region has a thickness in a range of 20 microns and 50 microns.

16. A system, comprising:
a micro discharge component, wherein the micro discharge component includes:
a non-conductive material;
a channel through at least a portion of the non-conductive material to receive a gas therethrough, having a first open end and a second open end;
a first electrode separated from a first circumferential position of the channel by a particular thickness of the non-conductive material between the first open end and the second open end;
a second electrode separated from a second circumferential position of the channel by a particular thickness of the non-conductive material between the first open end and the second open end;
a discharge region defined by a portion of the channel between the first electrode and the second electrode;
an optical emission collector positioned to receive an optical emission from the discharge region; and
a discharge shielding component between the discharge region from the optical emission collector;
a receiver configured to receive the optical emission from the optical emission collector and convert the optical emission into an electric signal; and
a computing device configured to receive the electric signal and determine a composition associated with the gas based on the electric signal.

17. The system of claim 16, wherein the discharge shielding component forms a seal preventing the gas from passing from the discharge region to the optical emission collector.

18. The system of claim 16, wherein the receiver includes a photodiode array including a plurality of photodiodes.

19. The system of claim 18, wherein each photodiode of the photodiode array is configured to:
receive a respective portion of the optical emission; and
convert the respective portion into a respective electric signal.

* * * * *